US010537512B2

(12) United States Patent
Dai et al.

(10) Patent No.: US 10,537,512 B2
(45) Date of Patent: Jan. 21, 2020

(54) MOISTURIZING COMPOSITION AND APPLICATION THEREOF IN PREPARATION OF MOISTURIZING COSMETIC PRODUCT

(71) Applicant: HUNAN YUJIA COSMETICS MANUFACTURING CO., LTD., Changsha, Hunan (CN)

(72) Inventors: Yuefeng Dai, Hunan (CN); Wenshu Kang, Hunan (CN); Guangwen He, Hunan (CN); Shaowei Yan, Hunan (CN)

(73) Assignee: HUNAN YUJIA COSMETICS MANUFACTURING CO., LTD., Changsha, Hunan (CN)

( * ) Notice: Subject to any disclaimer, the term of this patent is extended or adjusted under 35 U.S.C. 154(b) by 0 days.

(21) Appl. No.: 16/301,733

(22) PCT Filed: Apr. 3, 2018

(86) PCT No.: PCT/CN2018/081689
§ 371 (c)(1),
(2) Date: Nov. 15, 2018

(87) PCT Pub. No.: WO2018/184516
PCT Pub. Date: Oct. 11, 2018

(65) Prior Publication Data
US 2019/0282487 A1    Sep. 19, 2019

(30) Foreign Application Priority Data
Apr. 6, 2017    (CN) .......................... 2017 1 0220950

(51) Int. Cl.
| | |
|---|---|
| *A61K 8/68* | (2006.01) |
| *A61K 8/14* | (2006.01) |
| *A61K 8/34* | (2006.01) |
| *A61K 8/44* | (2006.01) |
| *A61K 8/49* | (2006.01) |
| *A61K 8/55* | (2006.01) |
| *A61K 8/60* | (2006.01) |
| *A61K 8/64* | (2006.01) |
| *A61K 8/67* | (2006.01) |
| *A61Q 19/00* | (2006.01) |

(52) U.S. Cl.
CPC .................. *A61K 8/68* (2013.01); *A61K 8/14* (2013.01); *A61K 8/345* (2013.01); *A61K 8/44* (2013.01); *A61K 8/4946* (2013.01); *A61K 8/553* (2013.01); *A61K 8/60* (2013.01); *A61K 8/602* (2013.01); *A61K 8/64* (2013.01); *A61K 8/673* (2013.01); *A61K 8/675* (2013.01); *A61Q 19/007* (2013.01)

(58) Field of Classification Search
CPC . A61K 8/68; A61K 8/14; A61K 8/345; A61K 8/44; A61K 8/4946; A61K 8/553; A61K 8/60; A61K 8/602; A61K 8/64; A61K 8/673; A61K 8/675; A61Q 19/007
See application file for complete search history.

(56) References Cited

U.S. PATENT DOCUMENTS

| | | | |
|---|---|---|---|
| 2006/0275238 A1 | 12/2006 | Blasko-Begoihn et al. | |
| 2007/0003502 A1* | 1/2007 | Tanabe ................ | A61K 8/0212 424/70.13 |

FOREIGN PATENT DOCUMENTS

| | | |
|---|---|---|
| CN | 103655369 A | 3/2014 |
| CN | 104434768 A | 3/2015 |
| CN | 104546516 A | 4/2015 |
| CN | 104622765 A | 5/2015 |
| CN | 104721068 A | 6/2015 |
| CN | 104800096 A | 7/2015 |
| CN | 105030564 A | 11/2015 |
| CN | 105997614 A | 10/2016 |
| CN | 106963665 A | 7/2017 |
| JP | H11322575 A | 11/1999 |
| JP | 2002327168 A | 11/2002 |
| JP | 2004168763 A | 6/2004 |
| JP | 2005330257 A | 12/2005 |
| JP | 2015017053 A | 1/2015 |
| KR | 100853301 B1 | 8/2008 |

OTHER PUBLICATIONS

The Japanese 1st Office Action dated Nov. 5, 2019 for Japanese Application No. 2018-559218. English translation only.

* cited by examiner

*Primary Examiner* — Doan T Phan
(74) *Attorney, Agent, or Firm* — Yue(Robert) Xu; Apex Attorneys at Law, LLP

(57) ABSTRACT

A moisturizing composition and an application thereof in the preparation of a moisturizing cosmetic product; each component in the formulation cooperates with the others to jointly provide the effects of increasing the moisture content of the skin and reducing the loss of moisture of the skin; compared with the efficiency of using a single component or several components alone, the efficiency of the present invention is significantly increased, indicating that compounding each component at a proper ratio produces a synergistic effect, thereby improving moisturizing efficiency.

9 Claims, 2 Drawing Sheets

MOISTURIZING COMPOSITION AND APPLICATION THEREOF IN PREPARATION OF MOISTURIZING COSMETIC PRODUCT

CROSS REFERENCE TO RELATED APPLICATIONS

This application is a US National Phase application based upon PCT Application No. PCT/CN2018/081689, filed on Apr. 3, 2018, which claims the priority of Chinese Patent Application No. 201710220950.9, filed on Apr. 6, 2017, and titled with "MOISTURIZING COMPOSITION AND APPLICATION THEREOF IN PREPARATION OF MOISTURIZING COSMETIC PRODUCT", and the disclosures of which are hereby incorporated by reference.

FIELD

The present disclosure relates to the field of cosmetics technology, specifically to a composition (called here uni-Hydra) and use thereof in preparing moisturizing cosmetics.

BACKGROUND

In all cosmetic raw materials, humectants occupy a very important position. On the one hand, almost all cosmetic formulas are inseparable from humectants, which are one of the basic substances that make up cosmetics; on the other hand, humectants play an important role in the function and quality of cosmetics. People are no longer satisfied with grease skin care products of the past, but some refreshing moisturizing products.

Humectants are a class of hygroscopic compounds that absorb moisture from moist air. Humectants retain moisture by absorbing and retaining water. In the traditional cosmetics, raw materials having moisturizing functions are mainly divided into two categories, one type is humectant, such as glycerol and so on, which retains moisture through moisture absorption; the other type is nonpolar humectant, such as Vaseline, white mineral oil and so on, which forms a sealing oil film on the surface so as to reduce vaporization of moisture from the surface of skin, and moisture of underlying tissue can diffuse into the stratum corneum to further hydrate the stratum corneum to achieve the effect of retaining moisture.

In traditional cosmetics field, people unilaterally believe that dry skin is due to the lack of lipids on the surface of skin. Studies have shown that only applying grease to the surface of the skin does not make the skin soft. The real cause of dry skin is insufficient water in the stratum corneum. The stratum corneum controls the moisture of the outer skin and acts as a barrier. In order to maintain the skin's water balance, the stratum corneum should maintain a certain amount of moisture to counter the humidity changes of the external environment. To make the skin smooth, soft and elastic, the skin must maintain a certain moisture content, usually the moisture content of skin should be maintained at 10%~20%.

The deficiencies of conventional cosmetics for moisturizing are as follows:

1. Most of the moisturizing cosmetics on the market merely hydrate and retain moisture of the skin with polyol, such as glycerol and propanediol, but do not take fully consideration on locking moisture of the skin and long term nourishment.

2. Traditional cosmetics use non-polar humectants such as Vaseline, white mineral oil and the like, which form a layer of sealing oil film on the surface, leading to poor breathability of skin. Due to excessive oiliness, these products have poor feelings of use, increase the burden on the oily skin, which also may clog pores and lead to the risk of acne on skin.

3. Although some cosmetics on the market developed new technology on the basis of hydrating and retaining moisture, there is few cosmetic that aims at repairing the skin barrier in an all-round way and improving self-repairing and dynamic balance of hydrating and retaining moisture of the skin barrier.

4. In traditional cosmetics, some functional moisturizing ingredients are added, but the promotion of percutaneous absorption is not fully considered, so that many functional moisturizing ingredients stay on the surface of the skin and cannot enter the stratum corneum of skin to effectively stimulate the skin's moisture retaining ability. Under this condition, the skin cannot retain moisture for a long time, resulting in a waste of the cost of the functional ingredients of cosmetics.

Thus, moisturizing cosmetics having good moisture retaining properties is in need of being further developed.

SUMMARY

In view of the above, the technical problem to be solved by the present disclosure is to provide a composition and a use thereof for preparing moisture retention product.

The composition provided by the present disclosure consists of the following ingredients in parts by mass:

| Ingredient | Amount |
|---|---|
| Glycerol | 2~6 parts; |
| Butanediol | 2~6 parts; |
| Propanediol | 1~4 parts; |
| Betaine | 1~4 parts; |
| Allantoin | 0.05~0.5 part; |
| Trehalose | 0.01~2 part; |
| Oat glucan | 0.01~2 part; |
| Xylitol | 0.01~2 part; |
| Hyaluronic acid | 0.01~0.5 part; |
| Oligo hyaluronic acid | 0.01~0.5 part; |
| Chitosan oligosaccharide | 0.01~1 part; |
| Tremella polysaccharide | 0.01~1 part; |
| Nicotinamide | 1~3 parts; |
| Amino acid | 0.1~3 parts; |
| Repairing peptides | 0.01~0.05 part; |
| Panthenol | 0.05~0.5 part; |
| Ceramide liposome | 0.01~0.5 part. |

In some embodiments, the composition consists of the following ingredients in parts by mass:

| Ingredient | Amount |
|---|---|
| Glycerol | 2 parts; |
| Butanediol | 2 parts; |
| Propanediol | 1 parts; |
| Betaine | 1 parts; |
| Allantoin | 0.05 part; |
| Trehalose | 0.01 part; |
| Oat glucan | 0.01 part; |
| Xylitol | 0.01 part; |
| Hyaluronic acid | 0.01 part; |
| Oligo hyaluronic acid | 0.01 part; |
| Chitosan oligosaccharide | 0.01 part; |
| Tremella polysaccharide | 0.01 part; |
| Nicotinamide | 1 part; |
| Amino acid | 0.1 part; |
| Rrepairing peptides | 0.01 part; |
| Panthenol | 0.05 part; and |
| Ceramide liposome | 0.01 part. |

In some embodiments, the composition consists of the following ingredients in parts by mass:

| | |
|---|---|
| Glycerol | 6 parts; |
| Butanediol | 6 parts; |
| Propanediol | 4 parts; |
| Betaine | 4 parts; |
| Allantoin | 0.5 part; |
| Trehalose | 2 parts; |
| Oat glucan | 2 parts; |
| Xylitol | 2 parts; |
| Hyaluronic acid | 0.5 part; |
| Oligo hyaluronic acid | 0.5 part; |
| Chitosan oligosaccharide | 1 part; |
| Tremella polysaccharide | 1 part; |
| Nicotinamide | 3 parts; |
| Amino acid | 3 parts; |
| Rrepairing peptides | 0.05 part; |
| Panthenol | 0.5 part; and |
| Ceramide liposome | 0.5 part. |

In some embodiments, the composition consists of the following ingredients in parts by mass:

| | |
|---|---|
| Glycerol | 4 parts; |
| Butanediol | 4 parts; |
| Propanediol | 2.5 parts; |
| Betaine | 2.5 parts; |
| Allantoin | 0.25 part; |
| Trehalose | 1 part; |
| Oat glucan | 1 part; |
| Xylitol | 1 part; |
| Hyaluronic acid | 0.25 part; |
| Oligo hyaluronic acid | 0.25 part; |
| Chitosan oligosaccharide | 0.5 part; |
| Tremella polysaccharide | 0.5 part; |
| Nicotinamide | 2 parts; |
| Amino acid | 1.5 parts; |
| Rrepairing peptides | 0.03 part; |
| Panthenol | 0.25 part; and |
| Ceramide liposome | 0.25 part. |

The butanediol used in the present disclosure is 1, 3-butanediol.

The ceramide liposome provided by the present disclosure is prepared from the following raw materials in parts by mass:

| | |
|---|---|
| Ceramide | 3~8 parts; |
| Caprylic/capric triglyceride | 6~9 parts; |
| Candelilla wax | 14~21 parts; |
| Hydrogenated lecithin | 4~6 parts; |
| Cholesterol | 2~4 parts; |
| Alcohol | 5~7 parts; |
| Tween-60 | 5~6 parts; |
| Glycerol | 8~12 parts; |
| Water | 27~53 parts. |

In order to improve solubility of ceramide in oil, caprylic/capric triglyceride (Medium Chain Triglyceride oil, MCT oil) is used in the present disclosure as the liquid oil. In order to increase the stability, candelilla wax is chosen as the solid oil. Candelilla wax, which is also known as euphorbia cerifera wax, is solid oil extracted from the epidermis of the small candelilla shrub. In the present disclosure, the volume ratio of solid oil to liquid oil is 70:30 to 99.9:0.1; and preferably, the volume ratio of the solid oil to the liquid oil is 70:30.

In the present disclosure, the hydrogenated lecithin is used as the main surfactant, and Tween-60 is used as a cosurfactant, and cholesterol is used to support the liposome and stablize the structure.

A method for preparing the liposome provided by the present disclosure, comprising, at 90° C., mixing ceramide, caprylic/capric triglyceride, candelilla wax, hydrogenated lecithin, cholesterol and alcohol, and dissolving to obtain an oil phase;

mixing Tween, glycerol and water to obtain an aqueous phase; and at 90° C., mixing the oil phase with the aqueous phase, emulsifying at 5000 rpm for 5 min, homogenizing at 1000 bar for 3 times, filtering and drying to obtain the liposome.

The liposomes prepared from the formula and by the method provided by the present disclosure have a mean diameter of 347.6 nm.

Organics containing amino and carboxyl are collectively called amino acids, which are basic constituent units of macromolecular proteins with biological functions, and also are basic substances that consist proteins required by animal nutrition. The amino acid used in the present disclosure is a compound amino acid, which includes lysine, histidine, arginine, aspartic acid, threonine, serine, glutamic acid, proline, glycine, alanine, isoleucine, leucine, tyrosine and phenylalanine.

Chitosan is the only alkaline polysaccharide that naturally exists, which is a low molecular weight polymer that is formed by linking 2-acetamido-2-deoxy-β-D-glucose residue and 2-amino-2-deoxy-β-D-glucose residue at different proportions via β-1,4-glycosidic bond, having a polymerization degree n of 2~20. The chitosan oligosaccharide used in the present disclosure is a chitosan with low molecular weight, and the molecular weight of which is below 10 kDa. Preferably, carboxymethyl deacetylate chitosan oligosaccharide is used in the present disclosure.

Hyaluronic acid (HA) is a disaccharide straight-chain macromolecular acidic mucopolysaccharide that is formed by acetylglucosamine and glucuronic acid in a ratio of 1:1 (mole ratio) through glycosidic bonds, with a molecular weight between tens of thousands and millions of Daltons. There is a wealth of hydroxyl (—OH) in the HA molecule, so that the molecule has a powerful hydrophilicity and can combine with large amount of water, showing a good moisture retention property. The hyaluronic acid used in the composition of the present disclosure has a molecular weight of 2,100,000. The oligo hyaluronic acid is obtained by degrading the hyaluronic acid, and the molecular weight of which is not more than 10,000.

Oat glucan is a mucopolysaccharide, which is a high molecular polymer formed by linking β-D-pyranoglucoside through β(1-3) and β(1-4) glycosidic bonds, wherein β(1-4) glycosidic bond accounts for about 70% and β(1-3) glycosidic bond accounts for about 30%. The molecular weight rang is 5,300~257,200. Water soluble β-glucan is used in the present disclosure, wherein the ratio of β(1-3) glycosidic bond and β(1-4) glycosidic bond is 1:2.5~1:2.6.

The repairing peptide is purchased from the market, including hexapeptide-9, tripeptide-1, palmitoyl tetrapeptide-7, palmitoyl pentapeptide-4, palmitoyl tripeptide-1 and palmitoyl tripeptide-5. Wherein, hexapeptide-9 has a concentration of 150~250 ppm, tripeptide-1 has a concentration of 900~1100 ppm, palmitoyl tetrapeptide-7 has a concentration of 45~55 ppm, palmitoyl pentapeptide-4 has a concentration of 90~110 ppm, palmitoyl tripeptide-1 has a concentration of 90~110 ppm, and palmitoyl tripeptide-5 has a concentration of 250~350 ppm. The repairing peptides used in the present disclosure are purchased from Shenzhen Winkey Biology Technology Co., Ltd.

The biological polysaccharide (chitosan oligosaccharide, tremella polysaccharide, trehalose, oat β-glucan and hyaluronic acid) in the composition of the present disclosure has a good film-forming ability, which can form a "water-locking film" on the surface of skin to prevent the moisture loss in skin, achieving an effect of long-term moisturizing. The oligo hyaluronic acid from enzyme digestion can penetrate deeply into the corium layer. The adding of oat β-glucan can effectively inhibit the degradation of hyaluronic acid in skin and promote the synthesis of hyaluronic acid.

The repairing peptides in the formula can increase the number of neonatal cells, thicken the skin, and omni-directionally repair skin from the outside and inside, so that gradually restores the normal structure and physiological functions of the skin, improves skin quality and promotes skin regeneration.

The compound amino acid, vitamin B3 (nicotinamide) and vitamin B5 (D-panthenol), lecithin and ceramide in the formula improve activity of cell, promote skin metabolism and repair skin barriers omni-directionally.

The organic osmotic mediums (betaine, allantoin and chitosan oligosaccharide) in the formula are used as the core ingredients to constitute the skin transdermal therapeutic technology. The combination of betaine and allantoin protects the cell's osmotic balance through osmosis of the stratum corneum, thereby increasing the water content of the superficial skin. Chitosan oligosaccharide can form a semi-permeable membrane on the surface of skin, which not only has good air permeability, but also does not interfere with the excretion of epidermal waste and toxins. The free amino group of chitosan oligosaccharide can chelate heavy metals, block metal ions, and enhance the effect synergistically.

The ceramide is lipid-encapsulated by lecithin and cholesterol. The lecithin and cholesterol have good adhesion to sebum membrane of skin, improving the transdermal release of the encapsulated ceramide. The liposome promotes the penetration of ceramide into the stratum corneum to repair the bimolecular phospholipid membrane, and the release is efficient and permanent.

The composition provided by the present disclosure includes multi-dimensional moisturizing factors, so that it is named uniHydra.

The present disclosure provides use of the composition in preparing moisturizing cosmetics.

The present disclosure further provides a moisturizing cosmetic, which comprises the composition in the present disclosure.

In the moisturizing cosmetic, the mass fraction of the composition is 7.33%~38.05%.

The cosmetic provided by the present disclosure further comprises Carbomer U-20, arginine, preservative and fragrance.

The preservative is PHL.

The moisturizing cosmetics provided by the present disclosure are cosmetics for skin.

The cosmetics for skin are cleaning creams, toners, lotions, essences, creams or masks.

In some embodiments, the moisturizing cosmetic provide by the present disclosure consists of the following ingredients in parts by mass:

| | |
|---|---|
| Glycerol | 2%~6%; |
| Butanediol | 2%~6%; |
| Propanediol | 1%~4%; |
| Betaine | 1%~4%; |
| Allantoin | 0.05%~0.5%; |
| Trehalose | 0.01%~2%; |
| Oat glucan | 0.01%~2%; |
| Xylitol | 0.01%~2%; |
| Hyaluronic acid | 0.01%~0.5%; |
| Oligo hyaluronic acid | 0.01%~0.5%; |
| Chitosan oligosaccharide | 0.01%~1%; |
| Tremella polysaccharide | 0.01%~1%; |
| Nicotinamide | 1%~3%; |
| Amino acid | 0.1%~3%; |
| Rrepairing peptides | 0.01%~0.05%; |
| Panthenol | 0.05%~0.5%; |
| Ceramide liposome | 0.01%~0.5%; |
| Carbomer U-20 | 0.05%~0.5%; |
| Arginine | 0.05%~0.5%; |
| Preservative | 0.8%~1.2%; |
| Fragrance | 0.01%~0.03%; and |
| Balance | water. |

In some embodiments, the moisturizing cosmetic provide by the present disclosure consists of the following ingredients in parts by mass:

| | |
|---|---|
| Glycerol | 2%; |
| Butanediol | 2%; |
| Propanediol | 1%; |
| Betaine | 1%; |
| Allantoin | 0.05%; |
| Trehalose | 0.01%; |
| Oat glucan | 0.01%; |
| Xylitol | 0.01%; |
| Hyaluronic acid | 0.01%; |
| Oligo hyaluronic acid | 0.01%; |
| Chitosan oligosaccharide | 0.01%; |
| Tremella polysaccharide | 0.01%; |
| Nicotinamide | 1%; |
| Amino acid | 0.1%; |
| Rrepairing peptides | 0.01%; |
| Panthenol | 0.05%; |
| Ceramide liposome | 0.01%; |
| Carbomer U-20 | 0.05%; |
| Arginine | 0.05%; |
| Preservative | 0.8%; |
| Fragrance | 0.01%; and |
| Balance | water. |

In some embodiments, the moisturizing cosmetic provide by the present disclosure consists of the following ingredients in parts by mass:

| | |
|---|---|
| Glycerol | 6%; |
| Butanediol | 6%; |
| Propanediol | 4%; |
| Betaine | 4%; |
| Allantoin | 0.5%; |
| Trehalose | 2%; |
| Oat glucan | 2%; |
| Xylitol | 2%; |
| Hyaluronic acid | 0.5%; |
| Oligo hyaluronic acid | 0.5%; |
| Chitosan oligosaccharide | 1%; |
| Tremella polysaccharide | 1%; |
| Nicotinamide | 3%; |
| Amino acid | 3%; |
| Rrepairing peptides | 0.05%; |
| Panthenol | 0.5%; |
| Ceramide liposome | 0.5%; |
| Carbomer U-20 | 0.5%; |
| Arginine | 0.5%; |
| Preservative | 1.2%; |
| Fragrance | 0.03%; and |
| Balance | water. |

In some embodiments, the moisturizing cosmetic provide by the present disclosure consists of the following ingredients in parts by mass:

| Glycerol | 4%; |
| Butanediol | 4%; |
| Propanediol | 2.5%; |
| Betaine | 2.5%; |
| Allantoin | 0.25%; |
| Trehalose | 1%; |
| Oat glucan | 1%; |
| Xylitol | 1%; |
| Hyaluronic acid | 0.25%; |
| Oligo hyaluronic acid | 0.25%; |
| Chitosan oligosaccharide | 0.5%; |
| Tremella polysaccharide | 0.5%; |
| Nicotinamide | 2%; |
| Amino acid | 1.5%; |
| Rrepairing peptides | 0.03%; |
| Panthenol | 0.25%; |
| Ceramide liposome | 0.25%; |
| Carbomer U-20 | 0.25%; |
| Arginine | 0.25%; |
| Preservative | 1%; |
| Fragrance | 0.02%; and |
| Balance | water. |

A method for preparing the moisturizing cosmetic provided by the present disclosure, comprising, at 80~85° C., mixing water, glycerol, butanediol, propanediol, betaine, allantoin, trehalose, oat glucan, xylitol, hyaluronic acid, oligo hyaluronic acid, chitosan and tremella polysaccharide, stirring at 60 rpm for 30 min, and homogenizing at 8000 rpm for 3 min to fully dissolve the above ingredients;

adding Carbomer U-20 and arginine, stirring at 50 rpm for 25 min, and homogenizing at 5000 rpm for 2 min;

reducing the temperature to 45~50° C., adding nicotinamide, amino acid, repairing peptides and panthenol, and stirring at 50 rpm for 25 min; and adding ceramide liposome, lecithin, cholesterol, preservative, and fragrance successively, stirring at 50 rpm for 25 min, and cooling to room temperature to obtain the moisturizing cosmetic.

The room temperature is 10~30° C.

In the formula provided by the present disclosure, each ingredient cooperates with each other, collectively plays a role in improving moisture content of skin and decreasing skin moisture loss. Comparing with using single ingredient or a combination of some ingredients, the effect is notably significant, demonstrating that the combination of these ingredients in an appropriate proportion has a synergistic effect, so as to improve the moisture retention.

DETAILED DESCRIPTION

Figure 1:
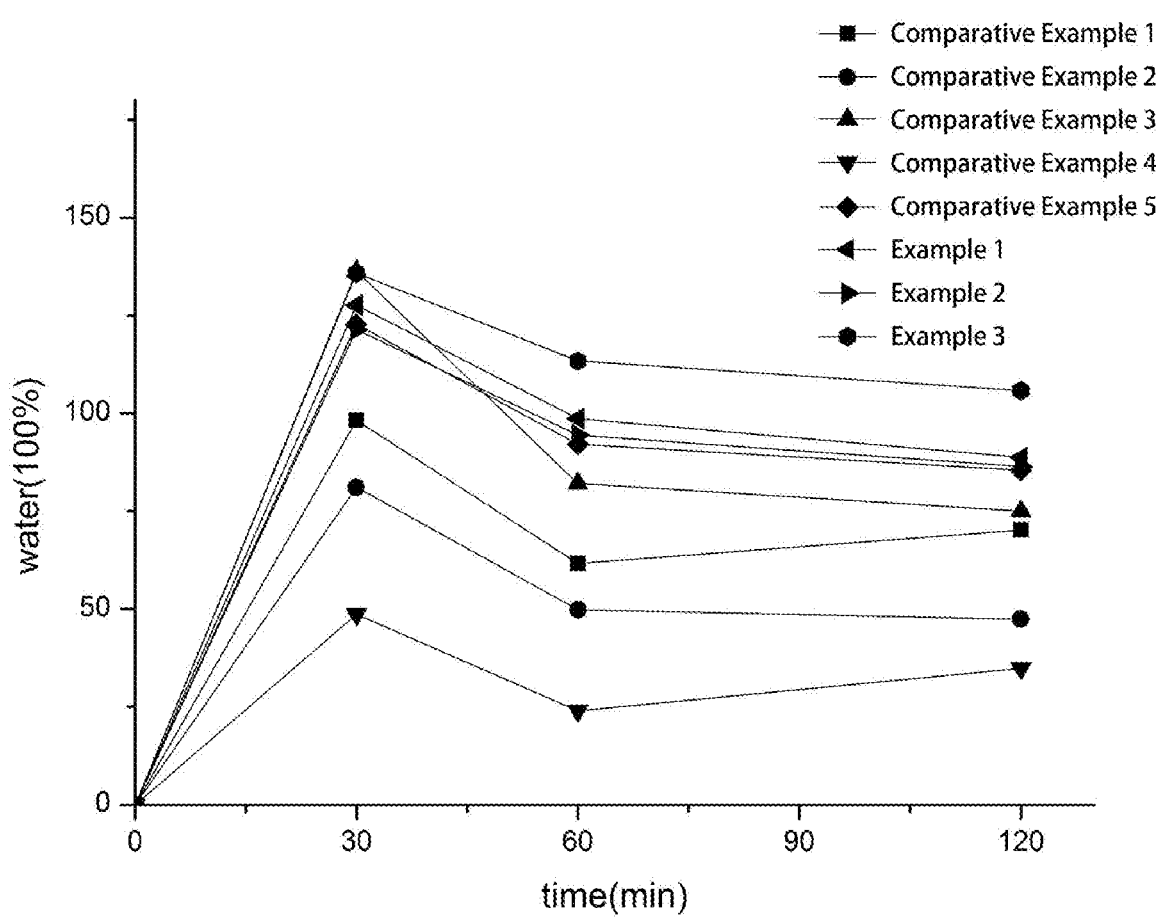
FIG. 1 shows effect of different test samples on the increasing ratio of moisture content of skin along time.

The present disclosure provides a composition, and a use thereof in preparing moisturizing cosmetics. One of ordinary skill in the art can learn from the contents of this document and appropriately improve the process parameters. It is to be noted that all such alternatives and modifications are obvious to one of ordinary skill in the art and are considered to be included in the present disclosure. The method and application of the present disclosure have been described in terms of preferred embodiments. It will be apparent to one of ordinary skill in the art that the methods and applications herein may be modified or modified in various ways without departing from the spirit and scope of the disclosure.

All the test materials used in the present disclosure are common commodities, which can be purchased on the market. The composition provided by the present disclosure contains multi-dimensional moisturizing factors, so called uniHydra.

The present disclosure will be illustrated in conjunction with examples hereinafter.

Preparing Liposomes of Examples 1~3

The formulas are shown in Table 1.

TABLE 1

| | Formulas of examples 1~3 | | | |
|---|---|---|---|---|
| Phase | Ingredient | Example 1 | Example 2 | Example 3 |
| Oil Phase | Ceramide | 3 g | 8 g | 5 g |
| | Caprylic/capric triglyceride | 6 g | 9 g | 7 g |
| | Candelilla Wax | 14 g | 21 g | 18 g |
| | Hydrogenated Lecithin | 4 g | 6 g | 5 g |
| | Cholesterol | 2 g | 4 g | 3 g |
| | Alcohol | 5 g | 7 g | 6 g |
| Aqueous Phase | Tween-60 | 5 g | 6 g | 5.5 g |
| | Glycerol | 8 g | 12 g | 10 g |
| | Water | 53 g | 27 g | 40.5 g |

To prepare the oil phase, ceramide, caprylic/capric triglyceride, candelilla wax, hydrogenated lecithin and cholesterol and alcohol were weighed according to proportions thereof, and heated to 90° C. to fully melt the oil. Thereafter, the mixture was well stirred. The temperature of oil phase was maintained at 90° C., and before emulsification, the lost alcohol was replenished.

To prepare the aqueous phase, Tween-60, glycerol and water were weighed according to proportions thereof, and heated to 90° C. to make Tween-60 fully dissolved in water. The temperature of the aqueous phase was maintained at 90° C., and before emulsification, the lost water was replenished.

The temperature of the oil phase was maintained at 90° C., and the 90° C.-aqueous phase was poured into the oil phase. The temperature was maintained at 90° C. A high-speed homogenizer was used to carry out the emulsification, and the condition was 5000 rpm for 5 min. After emulsification, the temperature was still maintained at 90° C.

Hot water was added to the high-pressure homogenizer firstly, then the feed pipe was heated to a temperature of 90° C. and the pressure was adjusted to 1000 bar. After the water totally entered the machine, the emulsion was added; and the emulsification was carried out at 1000 bar for 3 times.

The resultant was diluted 100 times and the particle diameter was measured. The results showed that the average particle diameter was 347.6 nm.

Preparing Cosmetics of Examples 4~6

The formulas are shown in Table 2.

TABLE 2

| | Formulas of examples 4~6 | | | |
|---|---|---|---|---|
| Phase | Ingredient | Example 4 | Example 5 | Example 6 |
| A | Water | 92.56 g | 57.95 g | 75.45 g |
| | Glycerol | 2 g | 6 g | 4 g |
| | Butanediol | 2 g | 6 g | 4 g |
| | Propanediol | 1 g | 4 g | 2.5 g |
| | Betaine | 1 g | 4 g | 2.5 g |
| | Allantoin | 0.05 g | 0.5 g | 0.25 g |
| | Trehalose | 0.01 g | 2 g | 1 g |

TABLE 2-continued

Formulas of examples 4~6

| Phase | Ingredient | Example 4 | Example 5 | Example 6 |
|---|---|---|---|---|
| | Oat glucan | 0.01 g | 2 g | 1 g |
| | Xylitol | 0.01 g | 2 g | 1 g |
| | Hyaluronic Acid (MW: 2,100,000) | 0.01 g | 0.5 g | 0.25 g |
| | Hyaluronic Acid (Oligomerization) | 0.01 g | 0.5 g | 0.25 g |
| | Chitosan Oligosaccharide | 0.01 g | 1 g | 0.5 g |
| | Tremella Polysaccharide | 0.01 g | 1 g | 0.5 g |
| B | Nicotinamide | 1 g | 3 g | 2 g |
| | Compound Amino Acid | 0.1 g | 3 g | 2 g |
| | Repairing peptides | 0.01 g | 0.05 g | 0.03 g |
| | Panthenol | 0.05 g | 0.5 g | 0.25 g |
| C | Ceramide liposome | 0.01 g | 0.5 g | 0.25 g |
| D | Carbomer U-20 | 0.05 g | 0.5 g | 0.25 g |
| | Arginine | 0.05 g | 0.5 g | 0.25 g |
| E | Caprylhydroxamic Acid PHL | 0.8 g | 1.2 g | 1 g |
| | Fragrance | 0.01 g | 0.03 g | 0.02 g |

The process was shown hereinafter.

1) The processing water in the reaction kettle was heated to 80~85° C., and ingredients of A phase were successively added. The mixture was stirred at 60 rpm for 30 min, and then homogenized at 8000 rpm for 3 min to fully dissolve the related ingredients.

2) D phase was added to the reaction kettle. The mixture was stirred at 50 rpm for 25 min and homogenized at 5000 rpm for 2 min to fully dissolve the related ingredients.

3) B phase was successively added to the reaction kettle. The mixture was stirred at 50 rpm for 25 min, and then the temperature was reduced to 45~50° C.

4) C phase and the E phase were successively added. The mixture was stirred at 50 rpm for 25 min, and then the temperature was reduced to room temperature to obtain the cosmetics.

Preparing Cosmetics of Comparative Examples 1~3

The formulas are shown in Table 3.

TABLE 3

Formulas of comparative examples 1~3

| Phase | Ingredients | Comparative Example 1 | Comparative Example 2 | Comparative Example 3 | Comparative Example 4 | Comparative Example 5 |
|---|---|---|---|---|---|---|
| A | Water | 75.45 g | 75.45 g | 75.45 g | 75.45 g | 75.45 g |
| | Glycerol | 8.01 g | — | — | — | 4.17 g |
| | Butanediol | 8.01 g | — | — | — | 5.57 g |
| | Propanediol | 5.01 g | — | — | — | 2.78 g |
| | Betaine | — | — | 6.77 g | 10.47 g | 0.42 g |
| | Allantoin | — | — | 0.68 g | 1.05 g | 0.01 g |
| | Trehalose | — | 6.58 g | — | — | 5.57 g |
| | Oat Glucan | — | 6.58 g | 2.71 g | — | 0.01 g |
| | Xylitol | 2.00 g | — | — | — | 0.01 g |
| | Hyaluronic Acid (MW: 2,100,000) | — | 1.65 g | — | — | 0.01 g |
| | Hyaluronic Acid (Oligomerization) | — | 1.65 g | 0.68 g | — | 0.01 g |
| | Chitosan Oligosaccharide | — | 3.29 g | — | 2.09 g | 0.01 g |
| | Tremella Polysaccharide | — | 3.29 g | — | — | 0.01 g |
| B | Nicotinamide | — | — | 5.42 g | — | 0.01 g |
| | Composited Amino Acid | — | — | 5.42 g | 8.37 g | 0.01 g |
| | Repairing peptides | — | — | — | — | 0.00 g |
| | Panthenol | — | — | 0.68 g | — | 2.92 g |
| C | Ceramide liposome | — | — | 0.68 g | 1.05 g | 1.53 g |
| D | Carbomer U-20 | 0.25 g | 0.25 g | 0.25 g | 0.25 g | 0.25 g |
| | Arginine | 0.25 g | 0.25 g | 0.25 g | 0.25 g | 0.25 g |
| E | Caprylhydroxamic Acid PHL | 1 g | 1 g | 1 g | 1 g | 1 g |
| | Fragrance | 0.02 g | 0.02 g | 0.02 g | 0.02 g | 0.02 g |

The process was shown hereinafter.

1) The processing water in the reaction kettle was heated to 80~85° C., and ingredients of A phase were successively added. The mixture was stirred at 60 rpm for 30 min, and then homogenized at 8000 rpm for 3 min to fully dissolve the related ingredients.

2) D phase was added to the reaction kettle. The mixture was stirred at 50 rpm for 25 min and homogenized at 5000 rpm for 2 min to fully dissolve the related ingredients.

3) B phase was successively added to the reaction kettle. The mixture was stirred at 50 rpm for 25 min, and then the temperature was reduced to 45~50° C.

4) C phase and the E phase were successively added. The mixture was stirred at 50 rpm for 25 min, and then the temperature was reduced to room temperature to obtain the cosmetics.

Efficacy Evaluation

Efficacy evaluation was performed between the moisturizing cosmetics purchased on the market and the moisturizing cosmetics prepared in the present disclosure. The evaluation was carried out according to the following method.

1. Method for Measuring the Moisture Measurement Value (MMV) of Skin 1.1 Principle of the Test Capacitance method was used to measure the moisture content in stratum corneum of human skin. The principle of the method is that, the dielectric constants of water and other substances were notably different, therefore, if the moisture contents of skin are different, the observed capacitance of skin are different, and the observed value can represent the skin moisture value.

1.2 Measurement Equipment

Multi-functional skin tester (CUTOMETER DUAL MPA 580, CK Company, Germany) was used, and in the experiments, moisture content of skin test probe and skin transepidermal water loss TEWL test probe were used.

1.3 Requirements for Measurement Conditions and Volunteers

Conditions of measurement environment: environment temperature of 22±1° C., humidity of 50±5%, and real-time dynamic detection.

Requirements for the volunteers: at least 30 valid volunteers, 16~65 years old (excluding pregnant and lactating women); the baseline of the skin moisture content in the testing region on forearm measured by capacitance method was between 15 and 100; without serious systemic diseases, immunodeficiency or autoimmune diseases; without active allergic diseases; without history of severe allergies to skin care cosmetics; without using hormonal drugs and immunosuppressive agents in the past month. In addition, the volunteers had not participated in other clinical trials during the test period and used the test samples according to regulations, and the information was complete. All volunteers have complete data and signed the informed consent form before the test.

1.4 Preparations Before the Test

2~3 days before the test, no product (cosmetics or external drugs) was allowed to apply on the testing region. Before the test, the inner sides of forearms of the subjects were cleaned and wiped with a dry facial tissue. After cleaning, the test regions were marked on the inner side of forearm. Before the measurement, the subjects sit in a room which met the requirement standard for at least 30 minutes without drinking water. Their forearms were exposed as in the test state, and kept relaxed.

1.5 Procedure of the Test

In the test, a testing region of 3×3 cm² was marked on the inner side of the left and right arms, and multiple regions might be marked on the same arm with an interval of 1 cm. The test samples and the blank control were randomly distributed on the left and right arms. Capacitive skin tester was used to perform the measurement on the testing regions and the control regions. Each area was measured 15 times in parallel. The basal value of each testing region was measured first, and then the test sample was evenly applied to the testing region with a latex finger sleeve at a dosage of 2.0±0.1 mg sample/cm². Moisture contents of skin in the testing region and the blank control region were measured after 1 hour, 2 hours and 4 hours (according to this time at the time of verification). The measurement of the same volunteer was performed by the same surveyor.

1.6 Analysis of Data

MMV values of different periods were respectively measured according to the design of the test.

$$W\% = (W1 - W0)/W0 \times 100\%$$ Formula of Calculation:

Comment: W %=increasing percentage of moisture measurement value (MMV)

W0=moisture content of skin before using the sample
W1=moisture content of skin after using the sample
The results were shown in Table 4 and FIG. 1

2. Method for Testing Transepidermal Water Loss (TEWL)

2.1 Principle of the Test

The measurement principle of the test instrument was derived from the Fick's law of diffusion: $dm/dt = D.A.dp/dx$. Two groups of temperature and humidity sensors were used to measure the water vapor pressure gradient formed by the transepidermal water loss at different testing regions near the epidermis (within 1 cm), so that the amount of water emitted from the percutaneous skin was directly measured. TEWL value is an important indicator of the skin barrier, and the lower the TEWL value of the skin is, the better the barrier function of the skin, and vice versa.

2.2 Requirements for Measurement Conditions and Volunteers

Conditions of measurement environment: environment temperature of 22±1° C., humidity of 50±5%, and real-time dynamic detection.

Requirements for the volunteers: at least 30 valid volunteers, 16~65 years old (excluding pregnant and lactating women); the baseline of the skin moisture content in the testing region on forearm measured by capacitance method was between 15 and 100; without serious systemic diseases, immunodeficiency or autoimmune diseases; without active allergic diseases; without history of severe allergies to skin care cosmetics; without using hormonal drugs and immunosuppressive agents in the past month. In addition, the volunteers had not participated in other clinical trials during the test period and used the test samples according to regulations, and the information was complete. All volunteers have complete data and signed the informed consent form before the test.

1.4 Preparations Before the Test

2~3 days before the test, no product (cosmetics or external drugs) was allowed to apply on the testing region. Before the test, the inner sides of forearms of the subjects were cleaned and wiped with a dry facial tissue. After cleaning, the test regions were marked on the inner side of forearm. Before the measurement, the subjects sit in a room which met the requirement standard for at least 30 minutes without drinking water. Their forearms were exposed as in the test state, and kept relaxed.

2.4 Processes of Measurement

In the test, a testing region of 3×3 cm² was marked on the inner side of the left and right arms, and multiple regions might be marked on the same arm with an interval of 1 cm. The test samples and the blank control were randomly distributed on the left and right arms. Capacitive skin tester was used to perform the measurement on the testing regions and the control regions. Each area was measured 15 times in parallel. The basal value of each testing region was measured first, and then the test sample was evenly applied to the

TABLE 4

MMV value of different periods

MMV (%)

| Time (min) | Comparative Example 1 | Comparative Example 2 | Comparative Example 3 | Comparative Example 4 | Comparative Example 5 | Example 4 | Example 5 | Example 6 |
|---|---|---|---|---|---|---|---|---|
| 0 | 0 | 0 | 0 | 0 | 0 | 0 | 0 | 0 |
| 30 | 98.19 | 81.15 | 136.20 | 48.69 | 122.76 | 127.66 | 121.36 | 135.81 |
| 60 | 61.62 | 49.80 | 82.05 | 24.04 | 92.14 | 98.67 | 94.44 | 113.37 |
| 120 | 70.11 | 47.42 | 74.96 | 34.80 | 85.43 | 88.71 | 86.36 | 105.76 | testing region with a latex finger sleeve at a dosage of 2.0±0.1 mg sample/cm². Moisture contents of skin in the testing region and the blank control region were measured after 1 hour, 2 hours and 4 hours (according to this time at the time of verification). The measurement of the same volunteer was performed by the same surveyor.

Analysis of Data

TEWL values of different periods were respectively measured according to the design of the test.

Formula of Calculation: $T\% = (T1-T0)/T0 \times 100\%$

Comment: T %=reducing percentage of skin transepidermal water loss (TEWL)
T0=moisture losing value of skin before using the sample
T1=moisture losing value of skin after using the sample
The results were shown in Table 5 and FIG. 2.

TABLE 5

TWEL values of different periods

| Time (min) | TWEL (%) | | | | | | | |
|---|---|---|---|---|---|---|---|---|
| | Comparative Example 1 | Comparative Example 2 | Comparative Example 3 | Comparative Example 4 | Comparative Example 5 | Example 4 | Example 5 | Example 6 |
| 0 | 0 | 0 | 0 | 0 | 0 | 0 | 0 | 0 |
| 30 | 7.80 | −4.77 | −0.69 | −3.07 | −1.08 | 10.77 | 11.48 | 12.41 |
| 60 | 12.90 | 8.80 | −0.98 | −2.17 | −9.99 | 11.81 | 11.79 | 13.47 |
| 120 | 13.36 | 7.83 | 0.89 | 5.56 | −10.63 | 13.96 | 14.56 | 17.92 |

Figure 2:
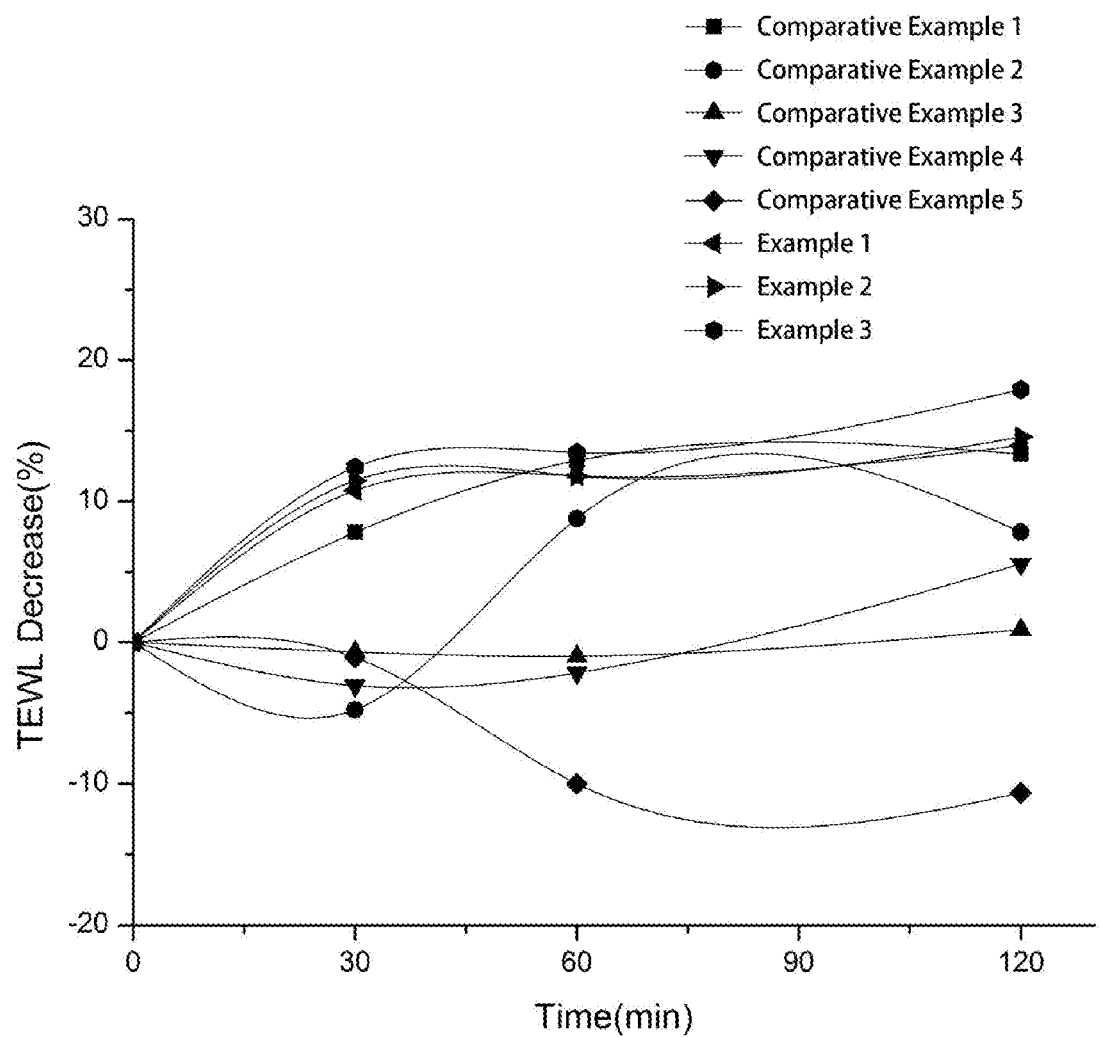
FIG. 2 shows effect of different test samples on the reducing ratio of skin moisture along time.

In combination of FIGS. 1~2 and tables 4~5, it could be concluded that the composition provided by the present disclosure has a scientific formulation, which can increase the real-time moisture content of skin by 135.81%, and maintain the moisture content of skin by an increase of 105.76% at 2 h. In addition, the composition shows an ability of greatly lowering skin moisture loss (TEWL), which helps the skin to be fully moisturized. Comparing with comparative examples 1~5, the formulas of examples 4~6 have significant effects ($p < 0.05$) on increasing moisture content and inhibiting moisture loss, indicating that the combination of the ingredients has a notably synergistic effect.

The above are merely preferred embodiments of the present disclosure. It should be noted that one of ordinary skill in the art can also make several improvements and refinements without departing from the principles of the present disclosure. These improvements and refinements should also be regarded as the scope of protection of the present disclosure.

What is claimed is:

1. A composition, consisting of the following ingredients in parts by mass:

| | |
|---|---|
| Glycerol | 2~6 parts; |
| Butanediol | 2~6 parts; |
| Propanediol | 1~4 parts; |
| Betaine | 1~4 parts; |
| Allantoin | 0.05~0.5 part; |
| Trehalose | 0.01~2 part; |
| Oat glucan | 0.01~2 part; |
| Xylitol | 0.01~2 part; |
| Hyaluronic acid | 0.01~0.5 part; |
| Oligo hyaluronic acid | 0.01~0.5 part; |
| Chitosan oligosaccharide | 0.01~1 part; |
| Tremella polysaccharide | 0.01~1 part; |
| Nicotinamide | 1~3 parts; |
| Amino acid | 0.1~3 parts; |
| Repairing peptides | 0.01~0.05 part; |
| Panthenol | 0.05~0.5 part; and |
| Ceramide liposome | 0.01~0.5 part. |

2. The composition according to claim 1, wherein the ceramide liposome is made from the following raw materials in parts by mass:

| | |
|---|---|
| Ceramide | 3~8 parts; |
| Caprylic/capric triglyceride | 6~9 parts; |
| Candelilla wax | 14~21 parts; |
| Hydrogenated lecithin | 4~6 parts; |
| Cholesterol | 2~4 parts; |
| Alcohol | 5~7 parts; |
| Polysorbate 60 | 5~6 parts; |
| Glycerol | 8~12 parts; and |
| Water | 27~53 parts. |

3. The composition according to claim 2, wherein the ceramide liposome is prepared by a method comprising:
at 90° C., mixing ceramide, caprylic/capric triglyceride, candelilla wax, hydrogenated lecithin, cholesterol and alcohol, and dissolving to obtain an oil phase;
mixing Polysorbate 60, glycerol and water to obtain an aqueous phase; and
at 90° C., mixing the oil phase with the aqueous phase, emulsifying at 5000 rpm for 5 min, homogenizing at 1000 bar for 3 times, filtering and drying to obtain the ceramide liposome.

4. A method for producing a moisturizing cosmetic, comprising adding the composition according to claim 1 in the moisturizing cosmetic.

5. A moisturizing cosmetic, comprising the composition according to claim 1.

6. The moisturizing cosmetic according to claim 5, wherein the mass fraction of the composition is 7.33%~38.05%.

7. The moisturizing cosmetic according to claim 5, further comprising Carbomer U-20, arginine, preservative and fragrance.

8. The moisturizing cosmetic according to claim 5, comprising:

| | |
|---|---|
| Glycerol | 2%~6%; |
| Butanediol | 2%~6%; |
| Propanediol | 1%~4%; |
| Betaine | 1%~4%; |
| Allantoin | 0.05%~0.5%; |

-continued

| | |
|---|---|
| Trehalose | 0.01%~2%; |
| Oat glucan | 0.01%~2%; |
| Xylitol | 0.01%~2%; |
| Hyaluronic acid | 0.01%~0.5%; |
| Oligo hyaluronic acid | 0.01%~0.5%; |
| Chitosan oligosaccharide | 0.01%~1%; |
| Tremella polysaccharide | 0.01%~1%; |
| Nicotinamide | 1%~3%; |
| Amino acid | 0.1%~3%; |
| Repairing peptides | 0.01%~0.05%; |
| Panthenol | 0.05%~0.5%; |
| Ceramide liposome | 0.01%~0.5%; |
| Carbomer U-20 | 0.05%~0.5%; |
| Arginine | 0.05%~0.5%; |
| Preservative | 0.8%~1.2%; |
| Fragrance | 0.01%~0.03%; and |
| Balance | water. |

9. A method for producing the moisturizing cosmetic according to claim 8, comprising, at 80~85° C., mixing water, glycerol, butanediol, propanediol, betaine, allantoin, trehalose, oat glucan, xylitol, hyaluronic acid, oligo hyaluronic acid, chitosan oligosaccharide and tremella polysaccharide, stirring at 60 rpm for 30 min, and homogenizing at 8000 rpm for 3 min to fully dissolve the above ingredients;

adding Carbomer U-20 and arginine, stirring at 50 rpm for 25 min, and homogenizing at 5000 rpm for 2 min;

reducing the temperature to 45~50° C., adding nicotinamide, amino acid, repairing peptides and panthenol, and stirring at 50 rpm for 25 min; and adding ceramide liposome, lecithin, cholesterol, preservative, and fragrance, stirring at 50 rpm for 25 min, and cooling to room temperature to obtain the moisturizing cosmetic.

* * * * *